US008728171B2

(12) United States Patent
Kaltenborn et al.

(10) Patent No.: US 8,728,171 B2
(45) Date of Patent: May 20, 2014

(54) ORTHOPEDIC FOOT PART

(71) Applicant: Otto Bock Healthcare GmbH, Duderstadt (DE)

(72) Inventors: Sven Kaltenborn, Duderstadt (DE); Felix Reuss, Duderstadt (DE); Sven Zarling, Duderstadt (DE); Bernhard Bischof, Duderstadt (DE); Thomas Kraus, Duderstadt (DE)

(73) Assignee: Otto Bock HealthCare GmbH, Duderstadt (DE)

( * ) Notice: Subject to any disclaimer, the term of this patent is extended or adjusted under 35 U.S.C. 154(b) by 46 days.

(21) Appl. No.: 13/625,942

(22) Filed: Sep. 25, 2012

(65) Prior Publication Data

US 2013/0024007 A1  Jan. 24, 2013

Related U.S. Application Data

(62) Division of application No. 12/365,924, filed on Feb. 5, 2009, now Pat. No. 8,298,294.

(30) Foreign Application Priority Data

Feb. 7, 2008 (DE) .......................... 10 2008 008 282

(51) Int. Cl.
*A61F 2/66* (2006.01)
(52) U.S. Cl.
USPC .................... 623/26; 623/47; 623/53; 623/50
(58) Field of Classification Search
USPC .......................... 623/24–27, 47–56
See application file for complete search history.

(56) References Cited

U.S. PATENT DOCUMENTS

| 6,443,993 | B1 | 9/2002 | Koniuk |
| 7,029,500 | B2 | 4/2006 | Martin |
| 2002/0138153 | A1 | 9/2002 | Koniuk |
| 2005/0192677 | A1 | 9/2005 | Ragnarsdottir |
| 2005/0197717 | A1 | 9/2005 | Ragnarsdottir et al. |
| 2006/0224247 | A1 | 10/2006 | Clausen et al. |
| 2006/0235544 | A1 | 10/2006 | Iversen |
| 2007/0027555 | A1 | 2/2007 | Palmer et al. |
| 2007/0043449 | A1 | 2/2007 | Herr et al. |
| 2008/0004718 | A1 | 1/2008 | Mosler |
| 2009/0030530 | A1 | 1/2009 | Martin |

FOREIGN PATENT DOCUMENTS

| DE | 696 12 838 | 11/2001 |
| DE | 10 2004 031 562 | 2/2006 |
| DE | 603 09 685 | 9/2007 |

(Continued)

*Primary Examiner* — Marcia Hoffman
(74) *Attorney, Agent, or Firm* — Whitham Curtis Christofferson & Cook, PC

(57) ABSTRACT

The invention relates to an orthopedic foot device with a connection part for the lower leg, a swivel joint (5) acting as an ankle joint (7) by means of which a foot part (10) is rotatably connected in the direction of dorsiflexion and the direction of plantar flexion to the connection part, with a damping arrangement (17) influencing the rotational movement about the swivel joint (5), with a sensor arrangement for detecting action states of the orthopedic foot part, and with a control unit connected to the sensor arrangement which controls the damping arrangement (17). The object is achieved by the fact that the sensor arrangement has an ankle-angle sensor which measures the angle between the connection part and the foot part (10), an absolute-angle sensor (20) relating to the plumb line and a moments sensor (21) for determining the torque on the ankle joint (7) or a force effecting a torque on the ankle joint (7).

15 Claims, 3 Drawing Sheets

(56) References Cited

FOREIGN PATENT DOCUMENTS

| | | |
|---|---|---|
| EP | 0810846 | 12/1997 |
| EP | 1570817 A1 | 9/2005 |
| JP | 2005-087347 | 7/2005 |
| JP | 2007524483 | 8/2007 |
| WO | 03/086245 | 10/2003 |
| WO | 2006/000211 | 1/2006 |
| WO | 2006112774 A1 | 10/2006 |
| WO | 2008/048658 | 4/2008 |
| WO | 2008/103917 | 8/2008 |

ORTHOPEDIC FOOT PART

This application is a divisional of U.S. patent application Ser. No. 12/365,924 filed Feb. 5, 2009, which issued as U.S. Pat. No. 8,298,294.

The invention relates to an orthopedic foot part with a connection part for the lower leg, a swivel joint acting as an ankle joint by means of which a foot part of the foot is rotatably connected in the direction of dorsiflexion and the direction of plantar flexion to the connection part, with a damping arrangement influencing the rotational movement about the swivel joint, with a sensor arrangement for detecting action states of the artificial foot, and with a control unit connected to the sensor arrangement which controls the damping arrangement. The invention also relates to a method for controlling such an orthopedic foot part.

It is known that the control unit of an orthopedic foot part, in the form of an artificial foot or foot orthotics, should satisfy a number of requirements to enable a safe use of the foot and enable the prosthesis wearer to have a motion sequence which is as natural as possible when walking. For example, during walking it is desirable for the foot part to allow a controlled impact on the standing plane when the heel impacts, and to allow a controlled heel-toe motion over the forefoot during which the body of the prosthesis wearer is slightly lifted. The natural foot undergoes dorsiflexion during the swing phase, resulting in a shortening of the leg-length, and hence an eased swing-through. Furthermore, safe standing on the artificial foot requires a high rigidity of the angle between the foot part and the connection part for the lower leg. However, the in this case expedient blocking of the swivel joint of the artificial foot, which swivel joint acts as the ankle joint, should be adjustable so that the prosthesis wearer can stand on inclined ground or in a shoe with a relatively high heel in a relaxed manner.

For example, US 2005/0197717 A1 discloses controlling the ankle angle during a gait cycle by means of an actuator in the form of a double-screw motor. In the process, a foot part is used which is intended to contribute to implementing an approximately natural gait by having a defined elasticity. Using an actuator in the form of a continuously driven motor requires a large amount of electrical energy which has to be supplied to the artificial joint. To this end, the prosthesis wearer must carry a powerful battery which must have a large volume and be heavy due to the required large capacity.

Furthermore, only controlling a damping of the rotational movement of the foot part relative to the connection part is known in order to satisfy some aspects of the control. To this end, U.S. Pat. No. 7,029,500 B2 discloses a special swivel joint as an ankle joint of the artificial foot, with the damping being influenced by a magneto-rheological liquid by virtue of the fact that applying a magnetic field makes it possible to switch the viscosity of the fluid from low to high, and hence the damping can be switched from low to high. This makes it possible to lock a dorsiflexion or plantar flexion which is automatically set during walking, and maintain it for a certain amount of time. This also makes it possible for the joint to be released when seated in order to set a plantar flexion setting which is also effected by the natural foot when seated.

Furthermore, US 2002/0138153 A1 discloses the use of a hydraulic arrangement for setting the rest angle when standing on inclined ground or for the different heel heights of a shoe used with the artificial foot, in which hydraulic arrangement the liquid flows from one liquid reservoir to the other in the case of a plantar flexion, and in the opposite direction for a dorsiflexion. An electromagnetic coil is inserted in a connecting line between the two liquid reservoirs and it controls the viscosity of the magneto-rheological liquid used as the hydraulic liquid; as a result of this, the damping can be switched between a first damping level and a second damping level. In order to satisfy the demanded control objectives, an inclination sensor for the lower leg part with respect to the perpendicular and a floor contact sensor are used. The floor contact sensor indicates that the artificial foot is experiencing a floor reaction force as a result of stepping on the floor.

The object of the present invention is to design an orthopedic foot part of the type mentioned initially which can be controlled in such a fashion that more demands on the properties of an orthopedic foot part can be satisfied than previously by means of an exclusively passive control for damping of the movement around the ankle joint.

According to the invention, this object is achieved in the case of an orthopedic foot part of the type mentioned initially by virtue of the fact that the sensor arrangement has an ankle-angle sensor which measures the angle between the connection part and the foot part, an absolute-angle sensor relating to the perpendicular and a moments sensor for determining the torque on the ankle joint or a force effecting a torque on the ankle joint.

It was found that using only the three sensor types makes it possible to control, in a desired fashion, the artificial foot, both during a gait cycle and whilst standing, by only acting on the damping of the movement of the ankle joint. As will be explained in more detail below, only a few sensor signals suffice to unambiguously determine the different required action states of the foot and to set the foot such that it mimics the movement of a natural, healthy foot during the gait cycle but nevertheless is able to impart a secure standing feeling whilst standing, even on inclined ground or with different heel heights. It was also found that the signals of the sensors provided according to the invention also suffice to be able to likewise reliably control routine gait situations, such as walking up and down stairs and ramps, and walking backwards.

In a preferred embodiment, the damping arrangement has damping means in the direction of plantar flexion, on the one hand, and in the direction of dorsiflexion, on the other hand, which are separate from one another and which can be controlled separately. Accordingly, the movements in both directions can be controlled separately. This makes it possible to treat the damping differently in the different rotational directions and, for example, treat it as a function of the output signal of the ankle-angle sensor.

In the case of the orthopedic foot part according to the invention, the foot part is designed to be wholly rigid or at least mostly rigid. The resilient movement of the foot part in the stance phase is implemented by controlling the damping of the rotational movement of the foot part relative to the connection part for the lower leg. For this purpose, it is necessary for the damping arrangement to be able be set in a plurality of intermediate states, preferably such that it can be adjusted in a continuous manner. The adjustment of the damping is controlled by an appropriate program in the control unit so that the movement of the foot part relative to the connection part for the lower leg is effected in a wholly controlled manner. This does not preclude the use of elastic parts to avoid impulsive transitions, e.g. using an elastic heel part to avoid an impulsive transition during the heel impact.

A variation results by virtue of the fact that, in a particularly preferred embodiment of the invention, the foot part comprises a rigid base part which is connected to the connection part via the ankle joint, and a forefoot part which is connected to the base part in a pivoting fashion. The forefoot part which is hinged on the front end of the base part in a pivoting fashion, mimics the movement of the toes around the toe joints in a natural foot, with the damping cylinder, which is controlled by both valves, being hinged on the one side to the connection part for the lower leg and on the other side to the forefoot part in the vicinity of the swivel joint between the base part and forefoot part. Depending on the angular position of the forefoot part, this, to a greater or lesser extent, results in reduced transfer of the damping effect of the damping cylinder onto the rotational movement of the base part relative to the connection part for the lower leg. In other words, the length of the lever of the base part affecting the ankle joint changes as the forefoot part bends, for example during the heel-toe motion in the stance phase of the gait cycle. This defined shortening of the lever length of the base part is taken into account by the program in the control unit.

Separate control of the damping means in the direction of plantar flexion, on the one hand, and the direction of dorsiflexion, on the other hand, makes it possible to fix a neutral position from which the movement in both directions is controlled. This neutral position can be manually fixed by means of a switch on the ankle joint. The switch can be a remotely-controlled switch so that it does not have to be actuated on the foot.

For example, it is expedient to set the neutral point in this manner if the carrier of the orthopedic foot part uses the latter with different shoes having different heel heights. Hence, this makes it possible to adapt to the new heel height in an unproblematic fashion by manually setting the neutral point. However, as an alternative, it is also possible that the neutral position can be identified from the sensor data by the control unit and that the damping means can be controlled starting from the neutral position.

In an embodiment preferred in practice, the damping arrangement is a hydraulic arrangement through which hydraulic liquid can flow and in which provision is preferably made for a dorsal valve to influence the flow in the direction of dorsiflexion and for a plantar valve to influence the flow in the direction of plantar flexion. Hence, in this preferred embodiment, the orthopedic foot part has two one-way valves through which the hydraulic liquid can in each case only flow in one direction and this makes it possible to separately control the movements in both directions.

A method according to the invention for controlling an orthopedic foot part which has a connection part for the lower leg, a swivel joint acting as an ankle joint by means of which a foot part of the foot is rotatably connected in the direction of dorsiflexion and the direction of plantar flexion to the connection part, a damping arrangement influencing the rotational movement about the swivel joint, a sensor arrangement for detecting action states of the artificial foot, and a control unit connected to the sensor arrangement which controls the damping arrangement, is, according to the invention, characterized in that a value proportional to the ankle moment occurring at the swivel joint, the ankle angle between the connection part and the foot part, and the absolute angle of the foot part with respect to the perpendicular are determined and in that the heel-toe motion of the foot in the stance phase of walking, the positioning of the foot part in the swing phase of walking, and the positioning and the movability of the foot part whilst standing are controlled by the damping arrangement as a function of said measured values. If no dorsiflexion follows a plantar flexion within a predetermined period of time, a change is made to standing.

Here, the damping in the direction of dorsiflexion and the damping in the direction of plantar flexion are preferably controlled separately by separate damping means. In the process, it is preferable that the damping means can be adjusted, preferably continuously, into a plurality of intermediate positions during the walking process. A program of the control unit for complete motion control carries out the adjustment which is preferably not effected by material elasticity. In this case, it is essential that the damping means can be adjusted taking into account the measured ankle angle or absolute angle.

The control unit for the foot motion according to the invention makes it possible to influence the parameters of a gait cycle by previously measured sensor signals for said gait cycle. Hence, the adaptation can be carried out immediately so that the parameters of a gait cycle do not—as is known from current active control units—have to be controlled by measured parameters from a preceding gait cycle. Thus, according to the invention, it is easily possible, for example, to determine a step length when the heel impacts the ground by taking into account the absolute angle of the foot part (or by taking into account the signal of the rotational angle sensor, also the connection part for the lower leg) and the measurement signal of the torque sensor, and to determine the damping parameters for the gait cycle which has just been initiated as a function of the determined step length. By way of example, the permissible rotational angles of the ankle joint in the direction of dorsiflexion and the direction of plantar flexion can be varied from a determined neutral point as a function of the determined step length. Limiting the rotational movement of the ankle joint is effected by a corresponding actuation of the respective damping means as a function of the measured ankle joint angle.

The combination of measurement signals according to the invention also makes it possible to distinguish between walking and standing by suitably evaluating these measurement signals in a processor of the control unit. Specifically, the transition from walking to standing is detected when the ankle moment, starting from a negative value, reaches a value in the vicinity of zero and the absolute value is equal to zero and remains unchanged. The lower leg or the centroid line of the body, respectively are on the plumb line when standing in a relaxed fashion. The transition from standing to walking is detected by virtue of the fact that the ankle moment is in the vicinity of zero, the absolute angle exceeds a threshold which differs from standing and the rate of change of the absolute angle exceeds a threshold. Here it is already possible to indirectly use the absolute angle measurement, which reproduces the forward-swinging motion of the leg when the walking starts, to determine the step length since the absolute angle occurring during the forward-swinging motion of the lower leg is proportional to the step length.

Moreover, the method according to the invention makes it possible to suitably control the artificial foot during the gait cycle; this will be explained in more detail below.

The described design of the artificial foot with a foot part, comprising a base part and a forefoot part which is connected to the base part in a pivoting manner, makes it possible to distinguish between the heel height of a shoe and a correspondingly inclined ground; this is not possible otherwise.

While the forefoot part remains in an extended position which is pre-stressed by a return spring if there is an inclined ground, a shoe with a high heel leads to a bent position of the forefoot part with respect to the base part. An additional angle sensor which reproduces the angular position of the forefoot part relative to the base part could therefore effect the distinction between "inclined ground" and "heel height".

If such a sensor is not provided, the fact that the heel height only has to be set when the shoe is put on can be accommodated by virtue of the fact that, at this moment in time, the control unit is provided with a signal which determines the neutral position of the swivel joint for the current standing state as a result of the heel height. Accordingly, a switch signal is provided for the control unit, which can preferably be transmitted to the control unit by the prosthesis carrier by means of a remote control device.

It is preferable for a hydraulic arrangement through which a hydraulic liquid flows to be used as the damping arrangement, with the damping means, which are provided for and controlled separately in the two movement directions, being formed by hydraulic one-way valves (plantar valve and dorsal valve).

By the way, the sensor arrangement used according to the invention makes it possible to determine the respective neutral point so that adaptation to the new neutral point can already be undertaken during the gait cycle itself.

In the following text, the invention is intended to be explained in more detail on the basis of an exemplary embodiment illustrated in the drawing, in which FIG. 1 shows a schematic illustration of a first exemplary embodiment of a foot prosthesis according to the invention;

Figure 1:
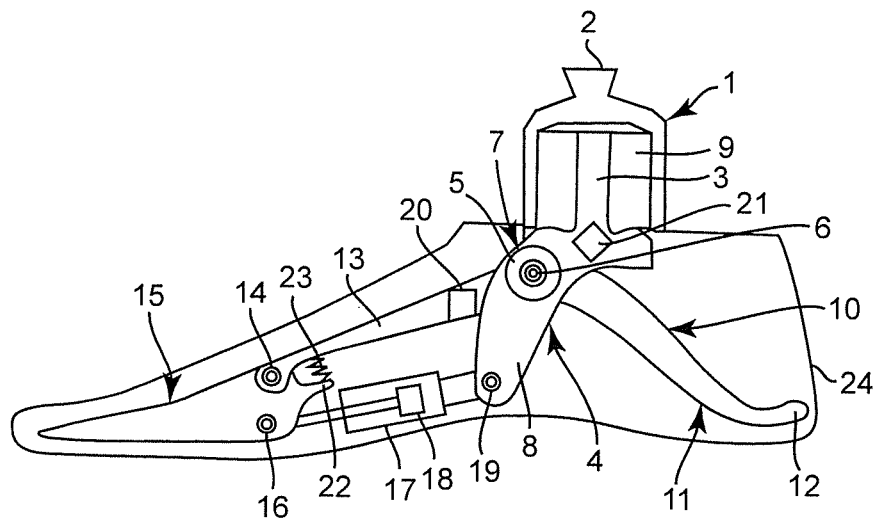

In the exemplary embodiment illustrated in FIG. 1, an attachment piece 1 is formed with an adjustment attachment 2 in the form of an upside-down pyramid frustum with four angled surfaces. The attachment piece 1 forms a pot which opens downwards and into which an upwardly pointing web 3 of a two-armed lever 4 extends. The two-armed lever can rotate about a swivel joint 5, the axis of rotation 6 of which simultaneously forms the axis of an ankle joint of the artificial foot. The swivel joint 5 is provided with an angle sensor 7. The two-armed lever 4 has a rigid attachment 8 which extends downwards.

The intermediate space formed by the web 3 in the pot of the attachment piece 1 which opens downwards is filled by a relatively stiff elastic material 9 so that the movement of the attachment piece 1 is transferred to the movement of the web 3 of the two-armed lever 4 with only a bit of damping. Accordingly, the attachment 8 moves like the attachment piece 1, but in a slightly damped fashion due to the elastic material 9.

The swivel joint 5 forming the ankle joint furthermore carries a main foot part 10, which a two-armed lever also extends into the heel region of the foot with a back lever arm 11, where the back lever arm 11, which runs obliquely backwards and downwards, is provided with an end 12, which is chamfered approximately horizontally.

The main foot part has a front lever arm 13 which extends towards the front from the ankle joint 5 and which extends forward, slightly obliquely downwards, in an almost straight line from the ankle joint 5 so that the main foot part 10 is designed such that it arches upwards towards the ankle joint 5 and drops obliquely, from the ankle joint 5, into the heel region towards the back and into a forefoot region towards the front, with the oblique drop into the heel region being steeper than the oblique drop into the forefoot region.

The front lever arm 13 of the main foot part 10 ends at the beginning of the forefoot region and carries a swivel joint 14 at that location, by means of which a forefoot part 15 replicating a toe region is rotatably hinged on the front lever arm 13 of the main foot part. The swivel joint 14 has an axis of rotation which runs horizontally, parallel to the axis of rotation 6 of the ankle joint 5. Since the forefoot part 15 mimics the toe region of a natural foot, its design towards the front is triangular and it tapers off. Below the swivel joint 14 there is a further swivel joint 16 on the forefoot part 15, by means of which a piston rod of a piston 18 of a hydraulic cylinder 17 is hinged on the forefoot part 15. The hydraulic cylinder 17 is rotatably hinged on the free end of the downwardly extending attachment 8 of the two-armed lever 4 by means of a swivel joint 19 so that the swivel joint 19 is arranged below the ankle joint 5 and is slightly offset towards the front (in the direction of the forefoot region 15) with respect to said ankle joint.

The ankle joint 5 comprises the angle sensor 7 for measuring the ankle angle, that is to say the angle between the web 3 (which is arranged flush with the lower leg) and the front lever arm 13 of the main foot part 10.

The front lever arm 13 of the main foot part 10 also carries an inclination sensor 20 which determines the inclination relative to the gravitational force (relative to the perpendicular). Such inclination sensors 20, which determine an absolute inclination angle relative to the gravitational acceleration, are known as acceleration sensor arrangements with or without a gyroscope.

The two-armed lever 4 comprises an ankle moment sensor which is flush with the adjustment attachment 2, i.e. flush with the (artificial) lower leg of the patient, and which measures the torque acting at said location.

At its back end, the forefoot part 15 is provided with a bearing attachment 22 used to hold a spring 23 which can be loaded with tension and pressure and which is supported at its other end on the front lever arm 13 of the main foot part 10. The spring 23 effects a return of the forefoot part 15 after dorsiflexion, the return velocity being determined by the hydraulic cylinder 17.

The hydraulic cylinder 17 can be designed as a passive actuator, in which the hydraulic flow effected by the piston 18 is controlled by valves (not illustrated), with it being possible to not only switch the valves on and off, but also to control them to have a defined flow rate. However, it is also possible to design the hydraulic cylinder 17 as an active actuator which can effect an adjustment of the forefoot part 15 without an external force acting.

Figure 2:
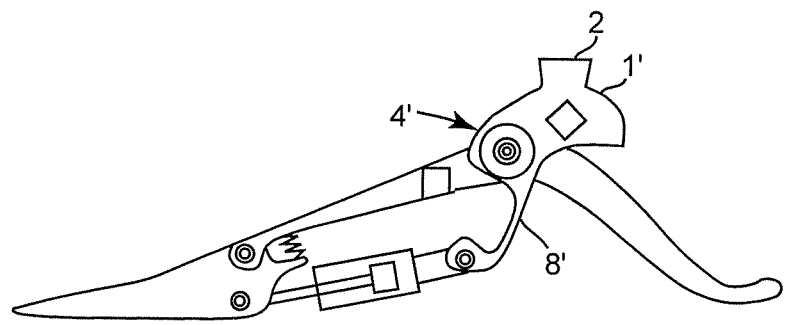
FIG. 2 shows a schematic illustration of a second exemplary embodiment of a foot prosthesis according to the invention.

The embodiment illustrated in FIG. 2 substantially corresponds to the embodiment in accordance with FIG. 1. One difference lies in the fact that the attachment piece 1' with the adjustment attachment 2 is designed integrally, so that elasticity formed by the elastic material 9 is no longer present. Instead, the downwardly extending attachment 8' of the two-armed lever 4' is designed with a thinning of the material so that the free end of the attachment, which carries the swivel joint 19, is arranged in a resilient manner with respect to the remaining material of the two-armed lever 4'.

It goes without saying that the artificial foot in accordance with the second embodiment also has a cosmetic cover 24, just like the first embodiment. However, this cosmetic cover 24 is not repeatedly illustrated for the second and third embodiment.

Figure 3:
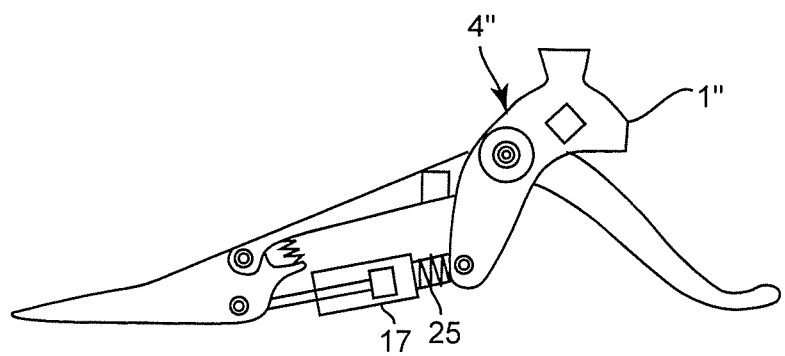
FIG. 3 shows a schematic illustration of a third exemplary embodiment of a foot prosthesis according to the invention.

In the case of the third embodiment of the artificial foot, illustrated in FIG. 3, the two-armed lever 4" and the adjustment attachment 2 are also designed integrally. The downwardly extending attachment 8 of the two-armed lever 4" is also rigid, just like in the first embodiment. Instead, the hydraulic cylinder 17 is elastically connected to the downwardly extending attachment 8 of the two-armed lever 4" by means of a coil spring 25. This realizes elasticity in series with the effect of the hydraulic cylinder 17, which elasticity is implemented by the elastic material 9 in the embodiment illustrated in FIG. 1 and by the resilient attachment 8' in the embodiment illustrated in FIG. 2. All other parts of the third embodiment correspond to those of the first embodiment.

Figure 4:
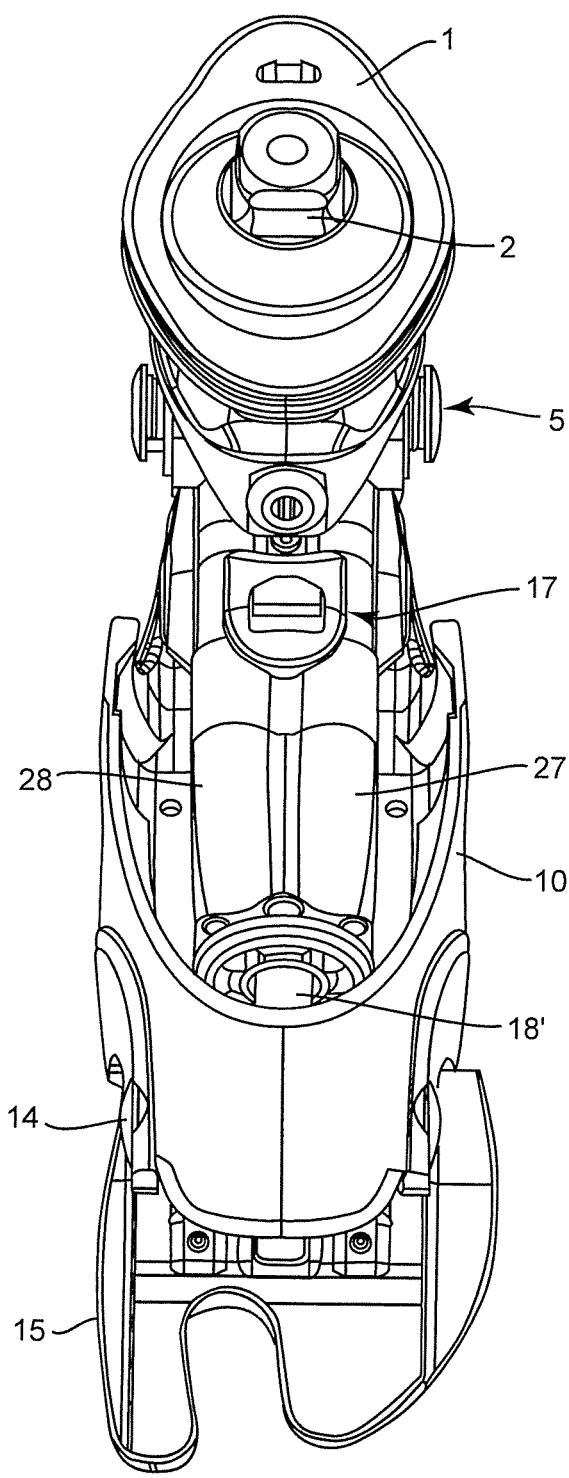
FIG. 4 shows a plan view of a structurally detailed further embodiment of a foot prosthesis according to the invention.
Figure 5:
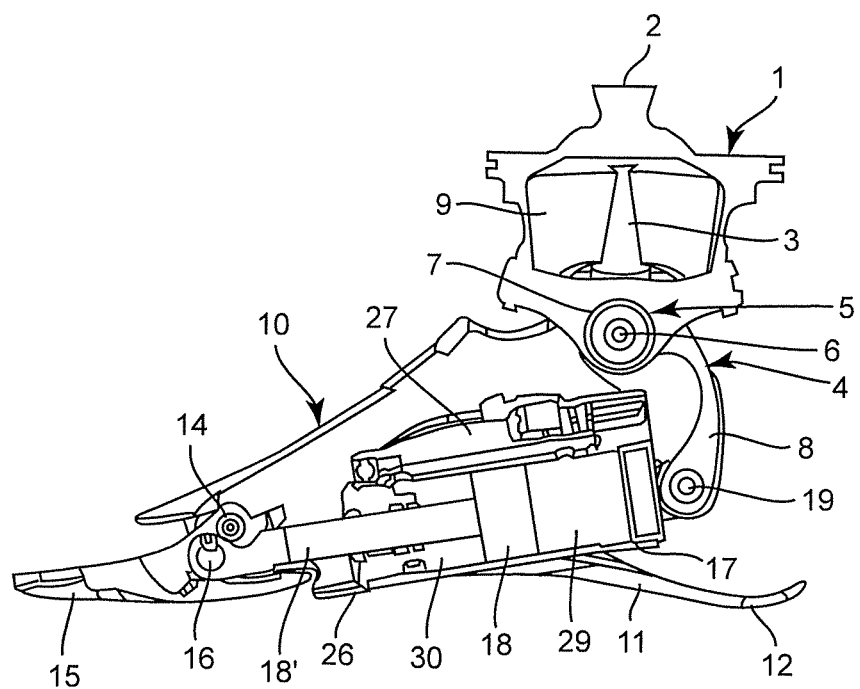
FIG. 5 shows a vertical section parallel to the sagittal plane through the foot prosthesis in accordance with FIG. 4.

The exemplary embodiment illustrated in FIGS. 4 and 5 reveals the attachment piece 1 with the pyramidal adjustment attachment 2. There is elastic material 9 in the attachment piece 1, and said elastic material 9 interacts in a damping fashion with the upwardly extending web 3 of the two-armed lever 4. In this exemplary embodiment, the downwardly extending attachment 8 of the two-armed lever 4 runs behind the ankle joint 5 in the walking direction and is, at that location, hinged to the hydraulic cylinder 17 via the swivel joint 19. The piston 18 moves in the hydraulic cylinder 17 such that it can be displaced longitudinally and can be led out via a bearing 26, located in the hydraulic cylinder 17, and connected to the further swivel joint 16 of the forefoot part 15. The ankle joint 5 furthermore serves to mount the main foot part 10 which in this case is in the form of a rigid housing and comprises an elastic lever 11 which is directed towards the back and serves as a heel lever. Hence, the foot part 10 and the heel lever 11 can together be pivoted around the ankle joint 5 and relative to the attachment piece 1 and the two-armed lever 4. The pivot movement between the attachment piece 1 and the foot part 10 is controlled and damped by the two-armed lever 4 and the hydraulic cylinder 17. Hinging the piston rod 18' of the piston 18 to the forefoot part 15 in this case only effects an additional control of the forefoot part 15 forming the toe plate and this, however, only slightly modifies the control of the main foot part 10 since the further swivel joint 16 is arranged in the direct vicinity of the swivel joint 14, between the forefoot part 15 and the main foot part 10. Two control valves 27, 28 are provided on the hydraulic cylinder 17 and they are arranged on the top side of the hydraulic cylinder 17. The control valves 27, 28 are connected to the chambers 29, 30 of the hydraulic cylinder 17 on both sides of the piston 18, with check valves (not illustrated) ensuring that the hydraulic liquid can only flow from the lower chamber 29 to the front chamber 30 as it passes through the first control valve 27, and this results in the insertion movement of the piston 18 into the hydraulic cylinder 17 being made possible and corresponding to plantar flexion of the main foot part 10 with respect to the attachment piece 1. The other control cylinder 28 only permits the hydraulic flow from the front chamber 30 to the back chamber 29 by means of check valves; as a result of this, the piston 18 can be pulled out of the hydraulic cylinder 17, i.e. the distance between the swivel joints 19, 16 is increased. This corresponds to dorsiflexion between the attachment piece 1 and the main foot part 10. At the same time, the displacement of the swivel joint 16 with respect to the swivel joint 14 effects a lifting of the forefoot part 15 towards the front.

In the illustrated embodiments, the artificial foot has the same method of operation. The sensor arrangement for measuring the ankle angle, the ankle moment and the absolute inclination angle makes it possible to determine the relevant functional states of the artificial foot and distinguish between them, the signal of the ankle-angle sensor being evaluated to determine, on the one hand, the ankle angle (between attachment piece 1, 1', 1" and the main foot part 10) and, on the other hand, the respective ankle angular velocity.

By way of example, it can be detected whether the artificial foot is used for walking or standing by determining the ankle angular velocity at the zero crossing of the ankle moment. If the ankle angular velocity is below a threshold during the zero crossing of the ankle moment, this is recognized as "standing" and the actuator in the form of the hydraulic cylinder 17 is set to have a high resistance by means of the valves such that a dorsal stop can be formed by said actuator.

A declining inclination or the heel height is determined by means of the inclination sensor 20 in the metatarsal region of the main foot part 10 during the zero crossing of the ankle moment.

If walking in the plane is detected, then the valve which is responsible for the plantar flexion of the foot is left in a half-open position while the valve which determines the dorsiflexion is closed with increasing ankle angle to form a dorsal stop.

If uphill walking is detected, an increased dorsiflexion of the forefoot part 15 is permitted.

If the heel impact after the swing phase and at the beginning of the stance phase is detected during walking by a negative ankle moment in particular, then the valve for the plantar flexion is controlled in such a manner that it closes with an increasing ankle angle in the direction of plantar flexion and hence forms a stop for the plantar flexion.

If a toe push-off is detected at the end of the stance phase (decreasing ankle moment in the case of an enlarged ankle angle), the valve for the dorsiflexion is completely opened after a dead time in order to initiate the lifting of the forefoot part (lifting of the toes) in the swing phase by means of an elastic element.

It can be seen from these examples that the important controls of an artificial foot during standing or walking can also be undertaken appropriately as a function of the floor inclination or heel height, with it already sufficing to control the movement resistance by means of the hydraulic cylinder. However, it is also possible to alternatively provide an active actuator in the sense of a valve.

The following modes of operation are implemented in the case of one exemplary embodiment for detecting the movement states of the foot prostheses and the control which results therefrom:

Distinguishing Standing-Walking

Walking and standing are distinguished according to the following criteria:

1. Detecting a swing phase

A swing phase is detected by virtue of the fact that the ankle moment is approximately zero since the foot is unloaded during the swing phase.

The absolute angle of the foot part 10 exceeds a threshold for standing, which can be individually defined. Furthermore, the absolute angular velocity exceeds a defined threshold.

2. Detecting a heel impact in the swung-forward state

A negative ankle moment (plantarflecting) is detected. The absolute-angle signal corresponds to that of a swung-forward foot compared to a threshold for standing which has been individually defined.

Optionally, a plantar flexion during the heel impact can be indicated by means of the ankle angular velocity.

3. Return to standing

After a detected heel impact, the absolute angle of the foot part 10 remains within a threshold value for standing which has been individually defined. As an alternative, or in addition, to this, an active reversal of the movement direction from dorsal to plantar in the central stance phase can be detected as a criterion for standing.

If standing has been detected, the control valves 27, 28 are set such that, for standing, this results in stops in the ventral and dorsal direction at a narrow angle (neutral position location). For the gait cycle, the stop is shifted in the dorsal direction and the damping properties for the plantar flexion and dorsiflexion are set as a function of the step length.

Distinguishing Plane-Ramp

The absolute angle measured at the beginning of the central stance phase in the gait cycle, that is to say after the entire foot has impacted on the ground, is greater than or less than a value range of the absolute angle which was defined for walking in the plane.

In accordance with the determined inclination of the ramp, the dorsal stop is changed and the damping properties during plantar flexion and dorsiflexion are set as a function of the absolute angle and the predicted step length.

Detecting Backward Motion

Backward motion is detected by detecting the back-swing phase and by detecting a forefoot impact in the backwardly extended state.

1. Detecting a back-swing phase

In the case of a measured ankle moment of approximately zero, the absolute-angle signal corresponds to a backwardly-extended foot (retroversion) compared to standing, and the absolute angular velocity exceeds a defined threshold.

2. Detecting the forefoot impact in the backwardly extended state

A relatively large positive ankle moment is measured.

Depending on the measured values, the stop is adjusted in the dorsal direction and the damping properties in plantar flexion and dorsiflexion are set as a function of the absolute angle during the forefoot impact.

Adaptation to Different Heel Heights

The heel height is preferably determined by reading the absolute-angle signal when a trigger signal is initiated manually. The neutral point for the control valves 27, 28 is set proportionally to the absolute angle.

As an alternative to this, the heel height, as opposed to a ramp inclination, can be determined in the case of an artificial foot with a forefoot part 15 attached in a hinged fashion by virtue of the fact that the angle of the forefoot part 15 is measured in relation to the main foot part 10. This is an additional option within the scope of the present invention.

Standing on Inclined Ground

In the case of a reversal of the movement direction from plantar to dorsal, the absolute angle is measured when the ankle moment undergoes a zero crossing. Accordingly, the dorsal stop for controlling the hydraulic cylinder 17 with the control valves 27, 28 is adjusted as a function of the ground inclination.

Detecting Walking on Stairs

The vertical distance travelled and the horizontal distance travelled by the main foot part 10 can be determined if the absolute-angle sensor 20 comprises two acceleration sensors for acceleration components in the direction of plumb line and the acceleration components can be output separately. The distances travelled are determined by integrating twice over the corresponding acceleration components. In these cases, walking up and down stairs can be distinguished and the stops for the damping properties during dorsiflexion and plantar flexion can be set appropriately.

The accelerations can be used in a similar manner to set walking at different walking velocities by correspondingly changing the stops in the dorsal direction and the damping properties during dorsiflexion and plantar flexion.

The invention claimed is:

1. Orthopedic foot device with a connection part for the lower leg, a swivel joint which acts as an ankle joint, a foot part rotatably connected to said swivel joint configured to rotate in a direction of dorsiflexion and a direction of plantar flexion relative to the connection part, a damping arrangement influencing rotational movement of said foot part about the swivel joint, a sensor arrangement for detecting action states of the foot part, and a control unit connected to the sensor arrangement which controls the damping arrangement, comprising within the sensor arrangement i) a torque sensor configured for measuring a torque of the ankle joint, ii) an angle sensor configured for measuring an ankle angle between the connection part and the foot part, and iii) an absolute-angle sensor configured for measuring an absolute angle of said foot part with respect to a plumb line, said control unit being configured to control exclusively by passive control said damping arrangement as a function of only said torque, said ankle angle, and said absolute angle respectively determined by said torque sensor, said angle sensor, and said absolute angle sensor each of i) heel-toe motion of said foot part in a stance phase of walking, ii) positioning of said foot part in a swing phase of walking, and iii) positioning and movability of said foot part whilst standing.

2. Orthopedic foot device according to claim 1, wherein the damping arrangement comprises separate damping means for damping in the direction of plantar flexion and in the direction of dorsiflexion, said separate damping means being configured to be controlled separately.

3. Orthopedic foot device according to claim 1, wherein the foot part is rigid.

4. Orthopedic foot device according to claim 1, wherein the foot part has a rigid body with an elastic heel part extending therefrom.

5. Orthopedic foot device according to claim 1, wherein the damping arrangement is settable in a plurality of intermediate states.

6. Orthopedic foot device according to claim 1, wherein the damping arrangement is adjustable in a continuous manner.

7. Orthopedic foot device according to claim 1, further comprising a switch configured to fix a neutral position of the ankle joint.

8. Orthopedic foot device according to claim 1, wherein the control unit is configured to identify a neutral position from the sensor data, and wherein the damping means is controlled starting from a neutral position.

9. Orthopedic foot device according to claim 8, wherein said switch is a remotely-controlled switch.

10. Orthopedic foot device according to claim 1, wherein the damping arrangement includes a hydraulic arrangement through which hydraulic liquid flows.

11. Orthopedic foot device according to claim 10, further comprising a dorsal valve to influence the flow of said hydraulic fluid in the direction of dorsiflexion and a plantar valve to influence the flow of said hydraulic fluid in the direction of plantar flexion.

12. Orthopedic foot device according to claim 1, wherein said control unit is configured for adjusting the damping arrangement until the swivel joint is blocked.

13. Orthopedic foot device according to claim 1 wherein said damping arrangement is configured to raise its damping value in a blocking direction as a maximum ankle angle is approached.

14. Orthopedic foot device according to claim 1, further comprising a return spring configured for effecting a return in said direction of dorsiflexion.

15. Orthopedic foot device according to claim 1 wherein said foot part includes a base part which is connected to the swivel joint and a forefoot part connected to said base part.

* * * * *